United States Patent
Paik et al.

(10) Patent No.: US 12,193,827 B1
(45) Date of Patent: Jan. 14, 2025

(54) METHOD AND APPARATUS FOR CLASSIFYING PATIENTS WITH BRAIN DISORDERS BASED ON ELECTRO ENCEPHALO GRAPHY (EEG) ANALYSIS

(71) Applicant: CHUNG ANG UNIVERSITY INDUSTRY ACADEMIC COOPERATION FOUNDATION, Seoul (KR)

(72) Inventors: Joon Ki Paik, Seoul (KR); Young Chul Youn, Seoul (KR); Min Jae Kim, Seoul (KR)

(73) Assignee: CHUNG ANG UNIVERSITY INDUSTRY ACADEMIC COOPERATION FOUNDATION, Seoul (KR)

( * ) Notice: Subject to any disclaimer, the term of this patent is extended or adjusted under 35 U.S.C. 154(b) by 0 days.

(21) Appl. No.: 18/390,698

(22) Filed: Dec. 20, 2023

(30) Foreign Application Priority Data

Jun. 29, 2023 (KR) .......................... 10-2023-0084064

(51) Int. Cl.
*A61B 5/372* (2021.01)
*A61B 5/00* (2006.01)
(Continued)

(52) U.S. Cl.
CPC ............ *A61B 5/372* (2021.01); *A61B 5/4088* (2013.01); *A61B 5/7264* (2013.01); *G16H 10/60* (2018.01); *G16H 50/20* (2018.01)

(58) Field of Classification Search
CPC ..... A61B 5/7267; A61B 5/4088; A61B 5/369; A61B 5/372; G16H 50/20; G16H 50/70; G06N 3/08
See application file for complete search history.

(56) References Cited

U.S. PATENT DOCUMENTS

2015/0088024 A1\* 3/2015 Sackellares ............ A61B 5/291
600/544
2019/0167179 A1\* 6/2019 Arzy .................... A61B 5/7475
(Continued)

FOREIGN PATENT DOCUMENTS

JP 2022505676 A 1/2022
KR 102366056 B1 2/2022
(Continued)

OTHER PUBLICATIONS

Notice of Preliminary Examination Results from Korean Intellectual Property Office dated Dec. 26, 2023 for KR Patent Application No. 10-2023-0084064.
(Continued)

*Primary Examiner* — Thaddeus B Cox
*Assistant Examiner* — Karen E Toth

(57) ABSTRACT

Disclosed are a method and an apparatus for classifying patients with brain disorders based on EEG analysis. The method for classifying patients with brain disorders based on EEG analysis includes: (a) receiving an EEG data set with a clinical diagnosis label, wherein the EEG data set includes a plurality of EEG signals and age information; (b) augmenting the EEG data set through a deep learning-based screening model, and augmenting the EEG signals and the age information in different schemes; (c) training the deep learning-based screening model to classify EEG data of patients into a target clinical diagnosis label by using the augmented EEG signals and age information; and (d) predicting a brain diagnosis label of brain disorders by applying EEG data of patients to the trained deep learning-based screening model.

8 Claims, 7 Drawing Sheets

(51) Int. Cl.
*G16H 10/60* (2018.01)
*G16H 50/20* (2018.01)

(56) References Cited

U.S. PATENT DOCUMENTS

| | | | | |
|---|---|---|---|---|
| 2023/0255564 A1* | 8/2023 | Pascual-Leone | .... | A61B 5/4088 600/301 |
| 2023/0277118 A1* | 9/2023 | Lucero | ................ | A61B 5/7267 600/544 |
| 2024/0156414 A1* | 5/2024 | Mishanin | ............. | A61B 5/0006 |

FOREIGN PATENT DOCUMENTS

| | | |
|---|---|---|
| KR | 102461646 B1 | 11/2022 |
| KR | 1020230076339 A | 5/2023 |
| KR | 1020230076399 A | 5/2023 |

OTHER PUBLICATIONS

Notice of Decision to Grant a Patent from Korean Intellectual Property Office dated Aug. 1, 2024 for KR Patent Application No. 10-2023-0084064.

\* cited by examiner

FIG. 3

| Abbreviation | Clinical diagnosis |
|---|---|
| *dementia* | dementia |
| *ad* | Alzheimer's disease dementia |
| *load* | late-onset Alzheimer's disease dementia |
| *eoad* | early-onset Alzheimer's disease dementia |
| *vd* | vascular dementia |
| *sivd* | subcortical ischemic vascular dementia |
| *ad-vd-mixed* | mix of Alzheimer's disease and vascular dementia |
| *mci* | mild cognitive impairment |
| *mci-ad* | mild cognitive impairment with amyloid PET positive |
| *mci-amnestic* | amnestic mild cognitive impairment |
| *mci-amnestic-ef* | amnestic mild cognitive impairment with encoding failure |
| *mci-amnestic-rf* | amnestic mild cognitive impairment with retrieval failure |
| *mci-non-amnestic* | nonamnestic mild cognitive impairment |
| *mci-multi-domain* | multi-domain mild cognitive impairment |
| *mci-vascular* | vascular mild cognitive impairment |
| *normal* | normal |
| *cb-normal* | community-based normal |
| *smi* | subjective memory impairment or cognitive decline |
| *hc-normal* | health care center normal |
| *ftd* | frontotemporal dementia |
| *bvftd* | behavioral variant frontotemporal dementia |
| *semantic-aphasia* | semantic aphasia |
| *non-fluent-aphasia* | non-fluent aphasia |
| *parkinson-synd* | Parkinson's syndrome |
| *parkinson-disease* | Parkinson's disease |
| *parkinson-dementia* | Parkinson's disease dementia |
| *nph* | normal pressure hydrocephalus |
| *tga* | transient global amnesia |

FIG. 4

| Data | Training | Validation | Test | Total |
|---|---|---|---|---|
| *Normal* | 367 | 46 | 46 | 459 |
| *MCI* | 334 | 42 | 41 | 417 |
| *Dementia* | 249 | 31 | 31 | 311 |
| Total | 950 | 119 | 118 | 1187 |

(a) CAUEEG-Dementia evaluation task

| Data | Training | Validation | Test | Total |
|---|---|---|---|---|
| *Normal* | 367 | 46 | 46 | 459 |
| *Abnormal* | 740 | 90 | 90 | 920 |
| Total | 1107 | 136 | 136 | 1379 |

(b) CAUEEG-Abnormal evaluation task

METHOD AND APPARATUS FOR CLASSIFYING PATIENTS WITH BRAIN DISORDERS BASED ON ELECTRO ENCEPHALO GRAPHY (EEG) ANALYSIS

CROSS-REFERENCE TO RELATED APPLICATION

This application claims under 35 U.S.C. § 119 (a) the benefit of Korean Patent Application No. 10-2023-0084064 filed on Jun. 29, 2023, the entire contents of which are incorporated herein by reference.

BACKGROUND

(a) Technical Field

The present disclosure relates to a method and an apparatus for classifying patients with brain disorders based on electro encephalo graphy (EEG) analysis.

(b) Background Art

Alzheimer's disease (AD) is the most common cause of dementia. Since there is no drug that treats or delays dementia symptoms, it is urgent to secure a reliable approach to finding dementia as early as possible.

Mild cognitive impairment (MCI) is an intermediate stage between healthy aging and dementia, and the annual conversion rate from MCI to Alzheimer's disease is 3 to 15%, especially the memory loss MCI is the most likely to be converted into Alzheimer's disease.

Recently, machine learning and deep learning techniques have been applied to discover Alzheimer's disease and MCI early, but these conventional techniques have a disadvantage in that a lot of time is required in a preprocessing process as handmade rules are used in the process of preprocessing to significantly reduce the amount of primitive EEG (Electro Encephalo Graphy) signals and purified ECG data is input.

SUMMARY OF THE DISCLOSURE

It is an object of the present disclosure to provide a method and an apparatus for classifying patients with brain disorders based on EEG analysis.

It is another object of the present disclosure to provide a method and an apparatus for classifying patients with brain disorders based on EEG analysis, which are applied to a deep learning-based model without a preprocessing process through handwork for patient EEG data to enable classification into normal, mild cognitive impairment, and dementia.

According to an aspect of the present disclosure, provided is a method for classifying patients with brain disorders based on electro encephalo graphy (EEG) analysis.

According to an embodiment of the present disclosure, a method for classifying patients with brain disorders based on electro encephalo graphy (EEG) analysis may be provided, which includes: (a) receiving an EEG data set input with a clinical diagnosis label of brain disorders, wherein the EEG data set includes a plurality of EEG signals and age information; (b) augmenting the EEG data set through a deep learning-based screening model, and augmenting the EEG signal and the age information in different schemes; (c) training the deep learning-based screening model to classify EEG data of patients into a target clinical diagnosis label by using the augmented EEG signal and age information, wherein the deep learning-based screening model includes a projection layer located between a final convolution layer and a classification layer on a backbone network; and (d) predicting a brain disorder diagnosis label by applying EEG data of a patient to the trained deep learning-based screening model.

The clinical diagnosis label of brain disorders may be for normal, mild brain disorders, and dementia.

Step (b) above may include randomly cropping the EEG signal to a fixed length T at a plurality of positions, and then normalizing the EEG signal by using an average and a standard deviation; augmenting the EEG signal by applying multiplicative white Gaussian noise (MWGN) and additive white Gaussian noise (AWGN) to the EEG signal; and augmenting the age information by applying the additive white Gaussian noise (AWGN) to the age information.

The augmented EEG signal and age information may be connected in an input layer through a single channel and applied to an encoder module, and the encoder module may generate a feature map by applying a convolution operation to the augmented EEG signal, and the age information may be connected in a feature map just before a fully connected layer of the encoder module.

The deep learning-based screening model may randomly crop the EEG signal based on an equation below:

$$\mathcal{L}_{crop}^{train}(f_w) = \frac{1}{BN}\sum_{i=1}^{B}\sum_{i=1}^{N}\ell(f_w(x_{t:t+T}^i), y^i) \simeq \frac{1}{N}\sum_{i=1}^{N}\ell\left(\underbrace{\frac{1}{M}\sum^{M}f_w(x_{t:t+T}^i)}_{test\text{-}time\ augmentation}, y^i\right)$$

wherein, B represents the number of training epochs, $x_{t:t+T}^i$ represents the EEG signal in which an i-th EEG signal in the EEG data set is cropped to a fixed length T, $y^i$ represents a clinical diagnosis label for $x_{t:t+T}^i$, l represents a loss function, N represents the amount of training data, and $f_w$ represents a model function having a parameter w.

Each of the EEG data set may be constituted by 21 channels, and include 19-channel EEG signals acquired at electrode positions of Fp1, F3, C3, P3, O1, Fp2, F4, C4, P4, O2, F7, T3, T5, F8, T4, T6, FZ, CZ, and PZ, a one-channel electrocardiogram signal, a one-channel photostimulation signal, and one-channel age information.

According to another aspect of the present disclosure, provided is an apparatus for classifying patients with brain disorders based on electro encephalo graphy (EEG) analysis.

According to an embodiment of the present disclosure, an apparatus for classifying patients with brain disorders based on electro encephalo graphy (EEG) analysis may be provided, which includes: (a) a data acquisition unit receiving an EEG data set input with a clinical diagnosis label, wherein the EEG data set includes a plurality of EEG signals and age information; a data augmentation unit augmenting the EEG data set, wherein the EEG signal and the age information are augmented in different schemes; a training unit training the deep learning-based screening model to classify EEG data of patients into a target clinical diagnosis label by applying the augmented EEG signal and the age information to the deep learning-based screening model, wherein the deep learning-based screening model includes a projection layer located between a final convolution layer and a classification layer on a backbone network; and a diagnosis prediction unit predicting a diagnosis label by applying EEG data of patients to the trained deep learning-based screening model.

The augmentation unit may randomly crop the EEG signal to a fixed length T at a plurality of positions, and then normalize the cropped EEG signal by using an average and a standard deviation, augment the EEG signal by applying multiplicative white Gaussian noise (MWGN) and additive white Gaussian noise (AWGN) to the EEG signal, and augment the age information by applying the additive white Gaussian noise (AWGN) to the age information.

The training unit may be trained such that the augmented EEG signal and age information is connected in an input layer through a single channel and applied to an encoder module, the encoder module may generate a feature map by applying a convolution operation to the augmented EEG signal, and the age information may be connected in a feature map just before a fully connected layer of the encoder module and classified into the target clinical diagnosis label.

According to an embodiment of the present disclosure, a method and an apparatus for classifying patients with brain disorders based on EEG analysis are provided, which are applied to a deep learning-based model without a preprocessing process through handwork for patient EEG data to enable classification into normal, mild brain disorders, and dementia.

BRIEF DESCRIPTION OF THE DRAWINGS

FIG. 3 is a diagram illustrating a diagnosis label according to an embodiment of the present disclosure.

FIG. 4 is a diagram illustrated for describing a configuration of the EEG data set according to an embodiment of the present disclosure.

DETAILED DESCRIPTION

Singular forms used in the present specification may include plural forms unless the context clearly indicates otherwise. In the present specification, a term such as "comprising" or "including," and the like should not be construed as necessarily including all various components or various steps disclosed in the present specification, and it should be construed that some component or some steps among them may not be included or additional components or steps may be further included. In addition, the terms "part', "module", and the like disclosed in the specification refer to a processing unit of at least one function or operation and this may be implemented by hardware or software or a combination of hardware and software.

Hereinafter, embodiments of the present disclosure will be described in detail with reference to the accompanying drawings.

Figure 1:
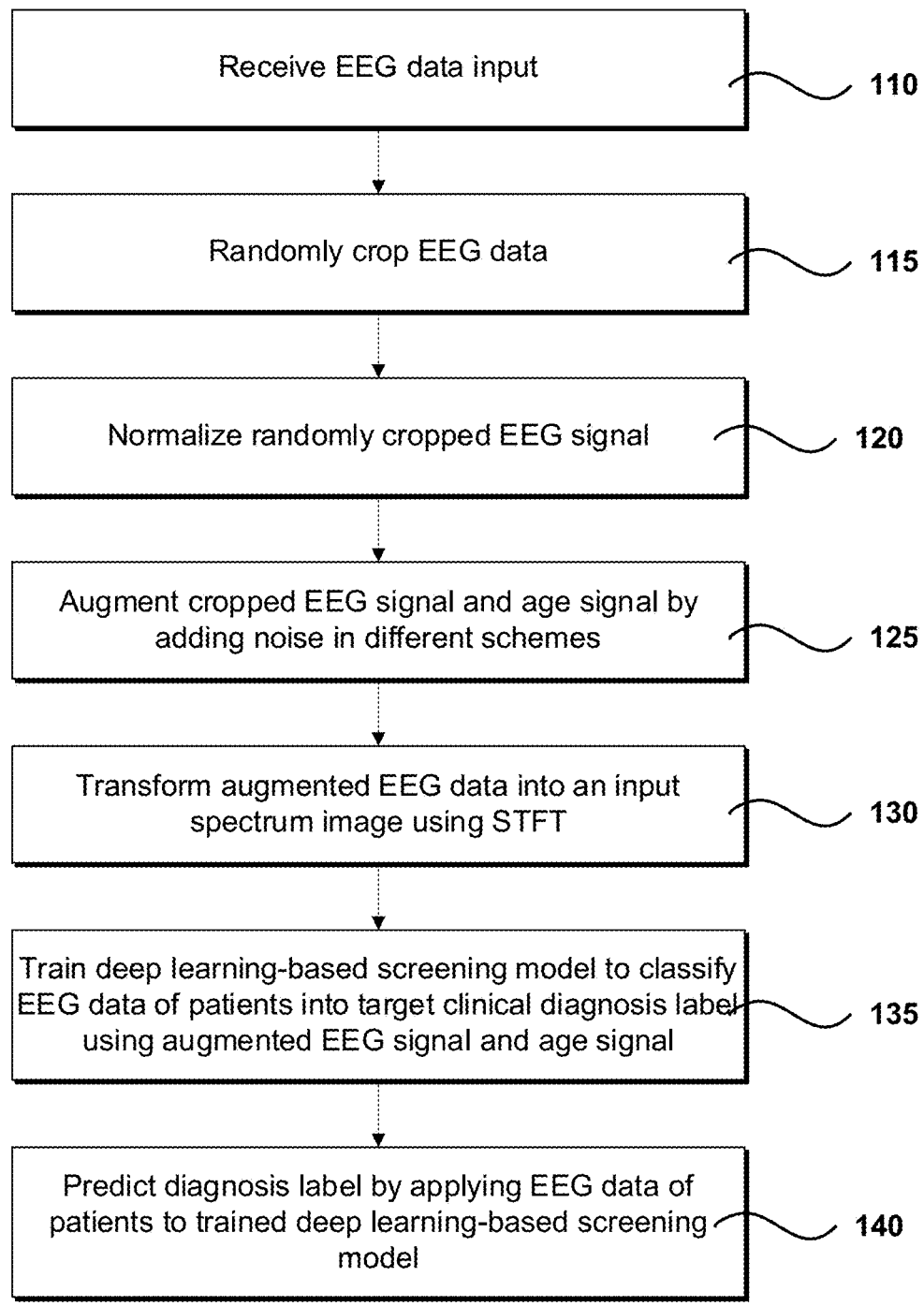
FIG. 1 is a flowchart illustrating a method for classifying patients with brain disorders based on EEG analysis according to an embodiment of the present disclosure.
Figure 2:
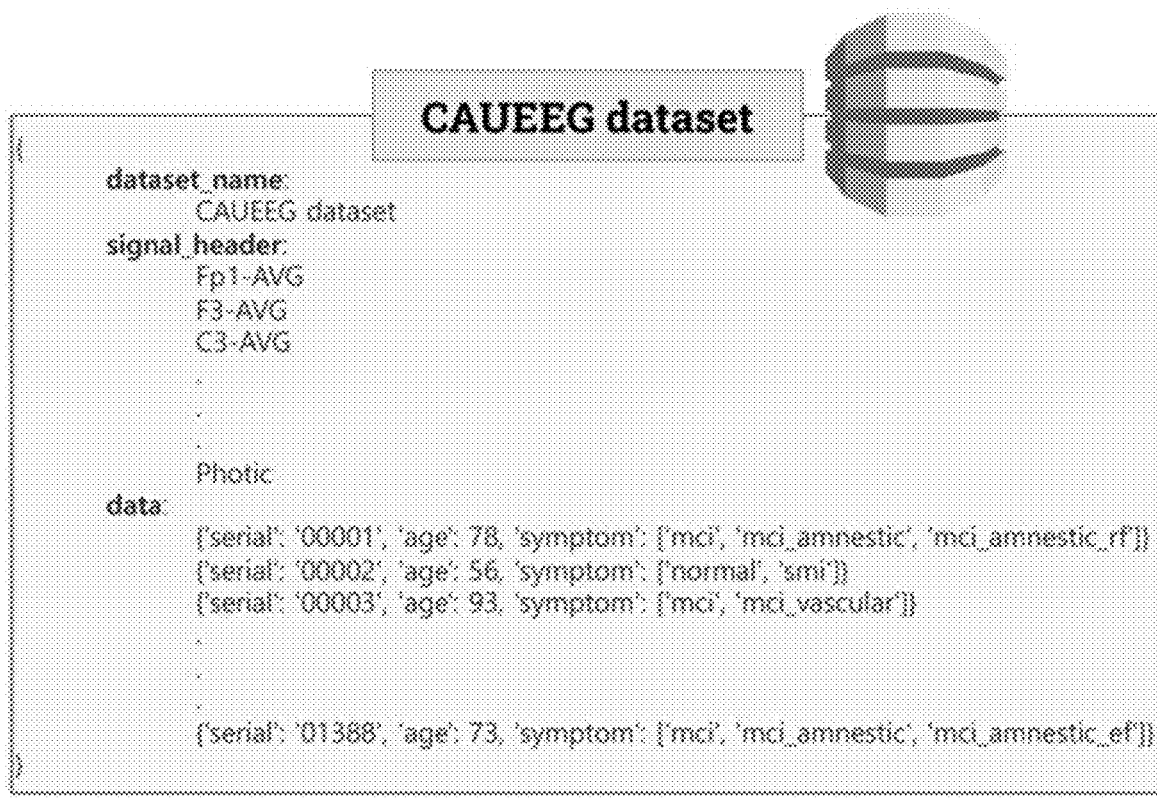
FIG. 2 is a diagram illustrating an EEG data set according to an embodiment of the present disclosure.
Figure 5:
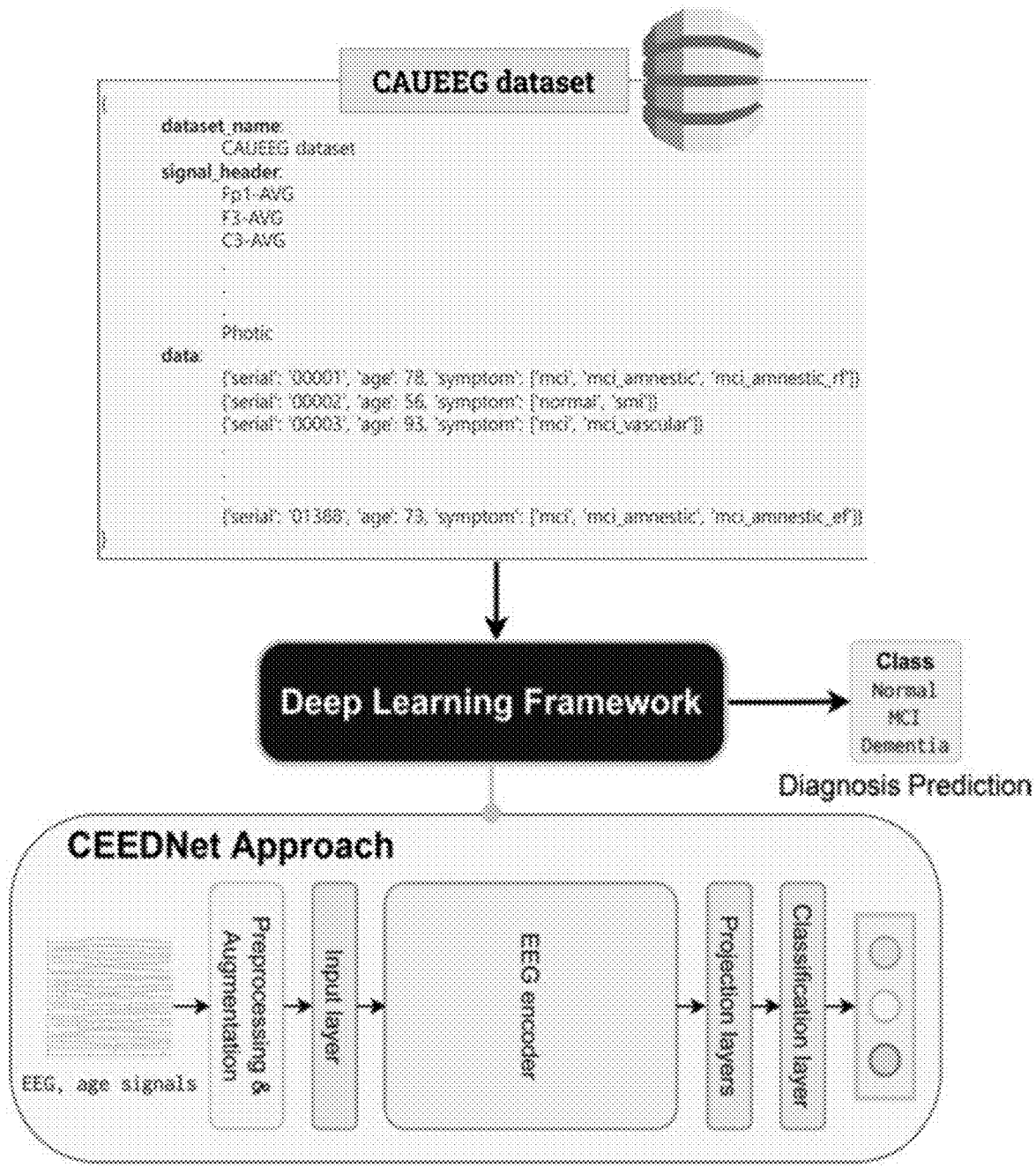
FIG. 5 is a diagram illustrating a configuration of a deep learning-based screening module according to an embodiment of the present disclosure.
Figure 6:
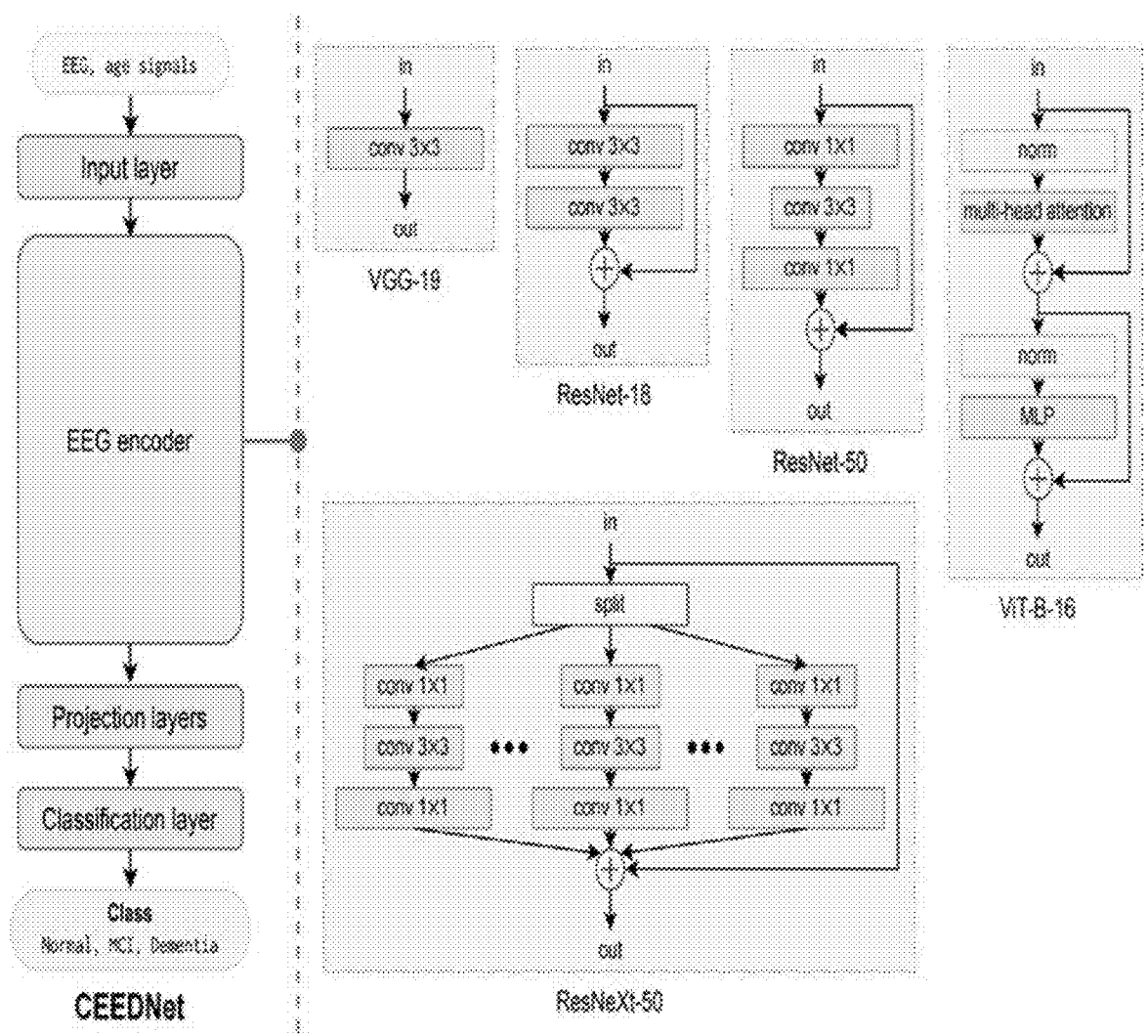
FIG. 6 is a diagram illustrating a configuration of an encoder module according to an embodiment of the present disclosure.

FIG. 1 is a flowchart illustrating a method for classifying patients with brain disorders based on EEG analysis according to an embodiment of the present disclosure. FIG. 2 is a diagram illustrating an EEG data set according to an embodiment of the present disclosure. FIG. 3 is a diagram illustrating a diagnosis label according to an embodiment of the present disclosure. FIG. 4 is a diagram illustrated for describing a configuration of the EEG data set according to an embodiment of the present disclosure. FIG. 5 is a diagram illustrating a configuration of a deep learning-based screening module according to an embodiment of the present disclosure. FIG. 6 is a diagram illustrating a configuration of an encoder module according to an embodiment of the present disclosure.

In step 110, an apparatus 100 for classifying patients with brain disorders receives electro encephalo graphy (EEG) data.

Here, the EEG data may include an EEG signal or age information having a clinical diagnosis label.

FIG. 2 illustrates one example of an EEG data set. This will be described in brief with reference to FIG. 2.

The EEG data set according to an embodiment of the present disclosure is a data set acquired from an actual patient. In other words, respective EEG data sets are acquired from 1155 patients from Aug. 24, 2012 to Mar. 12, 2020 at Chung-Ang University Hospital. Each EEG data set may be constituted by 12 channels. That is, 19 channels are EEG signals, and may be constituted by one electrocardiogram signal and one photostimulation signal.

EEG records may be acquired according to International 10-20 system (electrode position: Fp1, F3, C3, P3, O1, Fp2, F4, C4, P4, O2, F7, T3, T5, F8, T4, T6, Fz, CZ and PZ). The EEG signal is measured in a state in which a patient is awake with a comfortable state. After passing through an analog filter having a bandpass frequency of 0.5 to 70 Hz, the EEG signal is recorded as a sampling frequency of 200 Hz by using a digital brainwave system.

EEG data may be generated, which includes an event history, a patient age, and a diagnosis label generated while the EEG signal of the patient is recorded. A diagnosis label list is illustrated in FIG. 3.

As illustrated in FIG. 4, the EEG data set is constituted by an EEG signal with 459 normal diagnosis labels, 417 MCI diagnosis labels, and 311 dementia diagnosis labels, and the EEG data sets are randomly mixed, and then divided into training, verification, and test sets for each class at a ratio of 8:1:1.

Augmentation of the EEG data set described below is performed only in a training step of a deep learning-based screening model, and training of the deep learning-based screening model is completed, and then data augmentation may not be performed upon diagnosis prediction.

In step 115, the apparatus 100 for classifying patients with brain disorders augments the EEG data set.

According to an embodiment of the present disclosure, the augmentation of the EEG data set may be performed by the deep learning-based screening model.

Hereinafter, it should be appreciated that the augmentation of the EEG data set is performed by the deep learning-based screening model even if there is no separate description.

The EEG data set is remarkably less than a data set of another field due to EEG data characteristics. For example, ImageNet provides approximately one million image data, and LAION-400M provides approximately 400 million image-test pairs.

However, since the EEG data set is acquired from the patient, the EEG data set is bound to be remarkably less than a data set of a general image field, and for this reason, training of the deep learning-based screening model is also limited.

As a result, in an embodiment of the present disclosure, the deep learning-based screening model may be trained by augmenting the EEG data set. It should be appreciated that data augmentation described below may be performed only in the training step of the deep learning-based screening model, and after the training step is completed, the deep learning-based screening model is actually applied, so the data augmentation is not performed upon diagnosis classification prediction.

Recording times of the EEG signals acquired from the respective patients are different from each other. Accordingly, since the corresponding EEG signal is not suitable for extracting a feature value in the deep learning-based screening model, the corresponding EEG signal may be randomly cropped to a fixed length T. One EEG signal sequence may be randomly cropped to the fixed length T at a plurality of positions.

In an embodiment of the present disclosure, the description is based on the assumption that the EEG signal is randomly cropped at the plurality of positions (times) to the fixed length T, but the EEG signal may also be cropped in response to each event. For example, the EEG signal may also be cropped to the fixed length T to correspond to eye opening and eye closing events.

In an embodiment of the present disclosure, the description is based on the assumption that the EEG signal is randomly cropped to the fixed length T.

In relation to augmenting the EEG signal by randomly cropping it to the fixed length T, an objective function of a function $f_w$ having a parameter w in the deep learning-based classification model may be shown as in Equation 1:

$$\mathbb{E}_{crop}^{train}(f_w) = \int \frac{1}{N}\sum_{i=1}^{N} \ell\left(f_w(x_{t:t+T}^i), y^i\right) dp(t) \text{ for } t \sim \text{Uniform}(T_0, L^i - T),$$

[Equation 1]

wherein, $x_{t:t+T}^i$ represents the EEG signal in which an i-th EEG signal in the EEG data set is cropped to a fixed length T, $y^i$ represents a label for $x_{t:t+T}^i$, l represents a loss function, N represents the amount of training data, $T_0$ represents a start transition time, and $L^i$ represents a length of a signal of $x^i$.

An age signal is omitted for simplicity. Considering a transition time of a sensor upon starting, first 10 seconds are excluded in cropping ($T_0$=2000). t($T_0$, $L^i$−T) indicating that causes randomness in Equation 1 helps generalization through data augmentation. Since there is an integral that requires a lot of calculation cost in Equation 1, the deep learning-based classification model may be trained by using an approximate version instead of the integral.

The approximate version may be expressed as in Equation 2:

$$\mathbb{E}_{crop}^{train}(f_w) =$$

[Equation 2]

$$\frac{1}{BN}\sum^B\sum_{i=1}^N \ell\left(f_w(x_{t:t+T}^i), y^i\right) \simeq \frac{1}{N}\sum_{i=1}^N \ell\left(\underbrace{\frac{1}{M}\sum^M f_w(x_{t:t+T}^i)}_{\text{test-time augmentation}}, y^i\right)$$

wherein, B represents the number of training epochs, and Equation 2 shows test-time augmentation (TTA) in which random crop augmentation is M≥1 is naturally accepted. According to an embodiment of the present disclosure, M=8 or M=1 will be used in applying a TTA technique.

In step 120, the apparatus 100 for classifying patients with brain disorders normalizes the randomly cropped EEG signal.

For example, the apparatus 100 for classifying patients with brain disorders may normalize the EEG signal cropped to the fixed length T by using an average and a standard deviation calculated in a training set (z-score).

In step 125, the apparatus 100 for classifying patients with brain disorders augments the cropped EEG signal and age information by adding noise in different schemes. For example, the apparatus 100 for classifying patients with brain disorders may augment the EEG signal and the age information by adding random noise to the EEG signal and the age information by using two types of random noises based on a Gaussian distribution in which the average is 0.

The apparatus 100 for classifying patients with brain disorders may augment the cropped EEG signal by adding first random noise and second random noise to the EEG signal. That is, the cropped EEG signal may be augmented by adding multiplicative white Gaussian noise (MWGN) having a standard deviation such as $\sigma_{mwgn}$ which is in proportion to a signal gain. Further, the apparatus 100 for classifying patients with brain disorders may also add additive white Gaussian noise (AWGN) in which the standard deviation is $\sigma_{awgn}$ to the EEG signal to augment the EEG signal.

Further, the apparatus 100 for classifying patients with brain disorders may augment the age information by adding only the additive white Gaussian noise having the standard deviation as $\sigma_{awgn\_age}$.

The augmentation of adding the random noise may be considered only in the training step.

In step 130, the apparatus 100 for classifying patients with brain disorders transforms augmented EEG data into an input spectrum image by using STFT. Step 130 is applied when the deep learning-based screening model is a 2D model, and the corresponding step may not be performed when the deep learning-based screening model is a 1D model.

A hyper parameter of STFT may be used to make a result image in a square which is available in a space by starting at an input EEG sequence having the fixed length T.

$$\text{win\_len} = f\!f\!t\_len = \lfloor 2\sqrt{2T} + 0.5 \rfloor, \text{hop\_len} = \lfloor \text{win\_len}/4 + 0.5 \rfloor$$

Through this, an image having a space size in which H=⌊win_len/2⌋+1 and W=⌊T/hop_len⌋+1 is generated. For example, an image having a space resolution of 64×63 may be generated in an EEG sequence having a length of 2000. Here, an STFT preprocessing step is not applied to the 1D model.

In step 135, the apparatus 100 for classifying patients with brain disorders trains the deep learning-based screening model to classify the EEG data of patients into a target clinical diagnosis label by using the augmented EEG signal and age information.

A detailed configuration of the deep learning-based screening model is illustrated in FIG. 5.

In the deep learning-based screening model, as illustrated in FIG. 5, an augmentation unit is positioned at a front stage of an input layer, and the EEG data is randomly cropped, augmented at a plurality of positions by an augmentation module, and then delivered to an encoder module through the input layer.

As illustrated in FIG. 6, an encoder module may also be the 1D model, and also be the 2D model. According to an embodiment of the present disclosure, the deep learning-based screening model may be Simonyan and Zisserman (VGG), ResNet, ResNeXt, ViT, etc. as a backbone (i.e., the encoder module). Since the EEG data is multi-channel time-series data, the backbone does not necessarily need to be implemented as a 2D deep learning model. Such an encoder module may be a convolution-based backbone, and an operation of the convolution-based backbone is the same as a known operation. Hereinafter, only a different configuration will be described.

In an embodiment of the present disclosure, the 1D deep learning-based screening model may use VGG-19, ResNet-18, ResNet-50, and ResNeXt-50 as the backbone, the encoder module.

In addition, a 2D convolution layer of a backbone having a kernel size of k×k may be replaced with a 1D convolution having a kernel size of. A stride of each convolution stage may be equally set so that a sequence length of a last convolution is between 4 and 8.

The 2D model may be used by transforming the EEG data through short time Fourier transform (STFT) as described above.

Similar to the case of the 1D model, the stride of each convolution stage may be equally set such that an output feature map size of the last convolution step is between 4×4 and 8×8.

Since the age information is one of the most important risk factors of various symptoms including dementia, the age information may be input through the input layer together with the EEG signal.

A single channel field with the EGG signal and the age information may be connected together in the input layer, and the age information may be connected as a feature vector before a fully connected layer (network head).

In addition, a projection layer is located at a rear stage of the encoder module. The projection layer has more enhanced accuracy due to an additional feature projection layer instead of directly predicting a classification score after a last convolution stage. Therefore, 1 to 4 fully connected layers may be added between the last convolution (or attention) stage and the classification layer. Each added projection layer may reduce a dimension of a feature vector to a half.

According to an embodiment of the present disclosure, the deep learning-based screening model may provide a decision boundary which is similar to but smoother than ReLU by using Hendrycks and Gimpel (GELU) and Misra (Mish) as activation functions.

According to an embodiment of the present disclosure, as the deep learning-based screening model trains the deep learning-based screening module by randomly cropping and augmenting the EEG data at a plurality of positions (times) in the augmentation unit, the deep learning-based screening module may learn the same EEG data by calculating a potential vector at the plurality of positions and thus increase diagnosis classification prediction accuracy.

Further, the deep learning-based screening model according to an embodiment of the present disclosure is a model constituted by an ensemble of a plurality of different types of heterogeneous models, and performance and stability may be further enhanced through the ensemble of the heterogeneous models.

For example, a diagnosis class score s of the deep learning-based screening model for an EEG data sample $x^i$ may be estimated as in Equation 3:

$$s(x^i;w)=f_w(x_{t:t+T}^i) \text{ for } t \sim U(T_0, L^i-T), \quad \text{[Equation 3]}$$

wherein, t represents that a result $s(x^i;w)$ has a probabilistic attribute due to a random cropping process. A simple and efficient method for reducing the randomness of Equation 3 is a method using TTA. The TTA as a data perturbation ensemble technique widely used in a deep learning study is suitable for the EEG data. When the TTA is connected to Equation 3, a diagnosis class score estimation equation may be represented as in Equation 4:

$$\tilde{s}(x^i; w) = \frac{1}{M}\sum^M f_w(x_{t:t+T}^i) \text{ for } t \sim U(T_0, L^i-T) \quad \text{[Equation 4]}$$

Wherein, M>1 represents the number of randomly cropped EEG data samples. The TTA may enhance robustness of a deep learning-based screening model output by integrating multiple position estimations acquired by randomly cropping and enlarging the EEG data sample.

When a heterogeneous crossing model ensemble technique is used, a diagnosis class score s of a backbone model set W may be estimated as in Equation 5:

$$S(x^i; W) = \frac{1}{|W|}\sum_{w \in W} f_w(x_{t:t+T}^i) \text{ for } t \sim U(T_0, L^i-T), \quad \text{[Equation 5]}$$

wherein, |W| represents the number of a backbone model, and in an embodiment of the present disclosure, an ensemble of heterogeneous crossing models of 9 backbones (W={1D-VGG-19, 1D-ResNet-18, 1D-ResNet-50, 1D-ResNeXt-50-32×4d, 2D-VGG-19, 2D-ResNet-18, 2D-ResNet-50, 2D-ResNeXt-50-32×4d, and ViT-B-16}) is used.

When Equations 4 and 5 are combined, the class score may be estimated by using the TTA and the heterogeneous crossing model ensemble as in Equation 6.

$$\tilde{S}(x^i; W) = \frac{1}{|W|}\sum_{w \in W}\left(\frac{1}{M}\sum^M f_w(x_{t:t+T}^i)\right) \text{ for } t \sim U(T_0, L^i-T)$$

In step 140, the apparatus 100 for classifying patients with brain disorders applies the EEG data of the patient to the trained deep learning-based screening model to predict a diagnosis label.

Figure 7:
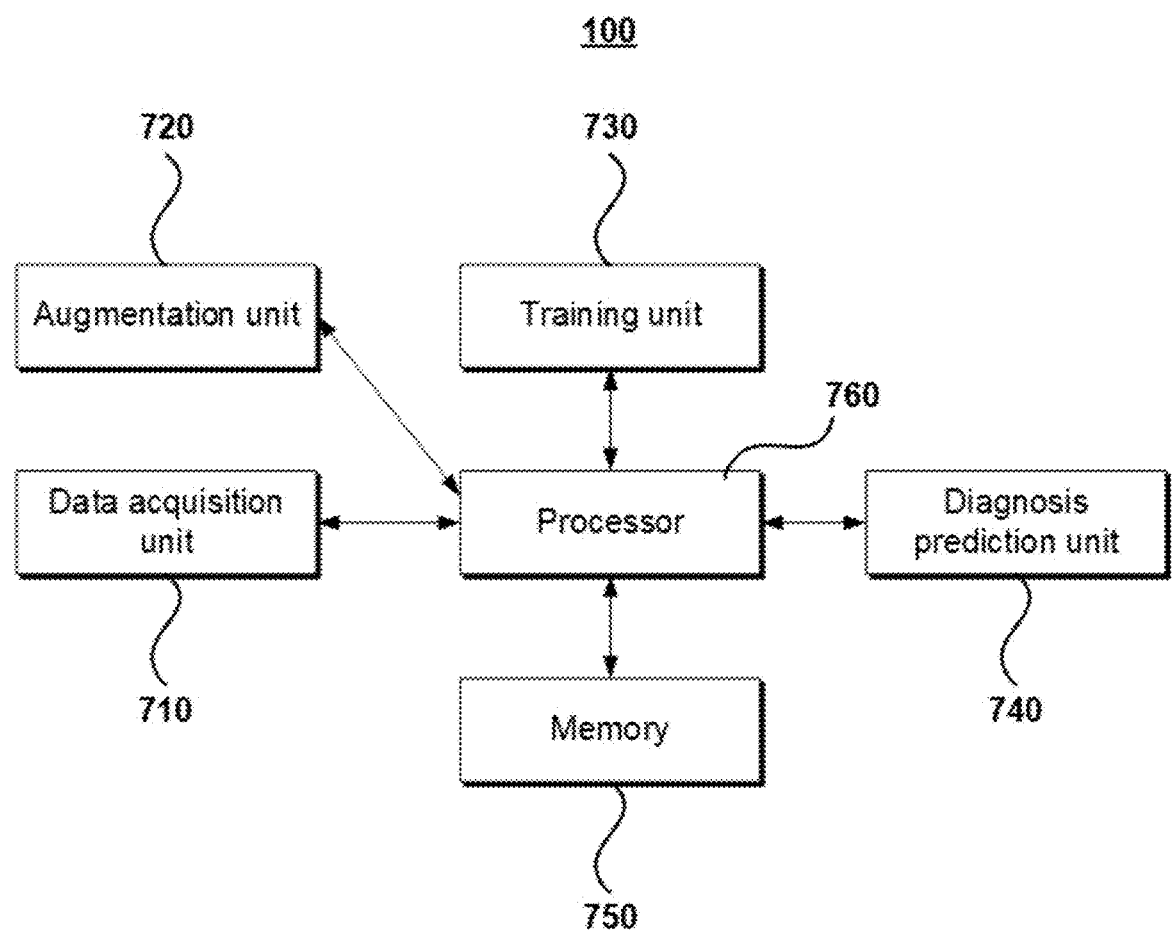
FIG. 7 is a block diagram schematically illustrating a configuration of an apparatus for classifying patients with brain disorders based on EEG analysis according to an embodiment of the present disclosure.

FIG. 7 is a block diagram schematically illustrating a configuration of an apparatus for classifying patients with brain disorders based on EEG analysis according to an embodiment of the present disclosure.

Referring to FIG. 7, the apparatus 100 for classifying patients with brain disorders according to an embodiment of the present disclosure is configured to include a data acquisition unit 710, an augmentation unit 720, a training unit 730, a diagnosis prediction unit 740, a memory 750, and a processor 760.

The data acquisition unit 710 is a means for acquiring EEG data. The EEG data may include an EEG signal and age information. The EEG signal may include 19 channels of EEG signals, one electrocardiogram signal, and one photo-stimulation signal.

Of course, the EEG data may include a clinical diagnosis label. When the EEG data is constituted by a training data set for training the deep learning-based screening module, the corresponding EEG data may include the clinical diagnosis label as a target clinical diagnosis label.

However, when diagnosis prediction is used by the deep learning-based screening module in which training of the EEG data is completed, it is natural that the EEG data may not include the clinical diagnosis label.

The augmentation unit 720 is a means for augmenting the EEG data. As described above, the augmentation unit 720 may augment the EEG signal and the age information. For example, the augmentation unit 720 may randomly crop the EEG signal to a fixed length T at a plurality of positions, and then normalize the cropped EEG signal by using an average and a standard deviation, and augment the EEG signal by applying multiplicative white Gaussian noise (MWGN) and additive white Gaussian noise (AWGN) to the EEG signal.

Further, the augmentation unit 720 may augment the age information by applying the additive white Gaussian noise (AWGN) to the age information.

The training unit 730 is a means for training the deep learning-based screening module by using the augmented EEG data. For example, the training unit 730 may train the deep learning-based screening module to classify the EEG data into a target clinical diagnosis label.

As described above, in the deep learning-based screening module, the augmented EEG signal and age information is connected to an input layer through a single channel and applied to an encoder module, and the encoder module may generate a feature map by applying a convolution operation to the augmented EEG signal. Further, the age information is connected in the feature map just before a fully connected layer of the encoder module to be used for training the deep learning-based screening module to classify the target clinical diagnosis label.

The diagnosis prediction unit 740 is a means for predicting the diagnosis label by applying the EEG data of the patent to the deep learning-based screening module of which training is completed.

The memory 750 is a means for storing instructions for performing a method for classifying patients with brain disorders based on EEG analysis according to an embodiment of the present disclosure.

The processor 760 is a means for controlling internal components (e.g., the data acquisition unit 710, the augmentation unit 720, the training unit 730, the diagnosis prediction unit 740, the memory 750, etc.) of the apparatus 100 for classifying patients with brain disorders according to an embodiment of the present disclosure.

The apparatus and the method according to embodiments of the present disclosure are implemented in a form of a program command which may be performed through various computer means and may be recorded in the computer readable medium. The computer readable medium may include a program command, a data file, or a data structure alone or in a combination thereof. The program command recorded in the computer readable medium may be specially designed and configured for the present disclosure, or may be publicly known to and used by those skilled in the computer software field. Examples of the computer-readable recording medium include magnetic media such as a hard disk, a floppy disk, and a magnetic tape, optical media such as a CD-ROM and a DVD, magneto-optical media such as a floptical disk, and a hardware device which is specifically configured to store and execute the program command such as a ROM, a RAM, and a flash memory. An example of the program command includes a high-level language code executable by a computer by using an interpreter and the like, as well as a machine language code created by a compiler.

The hardware device may be configured to be operated with one or more software modules in order to perform the operation of the present disclosure and vice versa.

Hereinabove, the present disclosure has been described with reference to exemplary embodiments thereof. It will be understood by those skilled in the art to which the present disclosure pertains that the present disclosure may be implemented in a modified form without departing from essential characteristics of the present disclosure. Therefore, the embodiments disclosed herein should be considered in an illustrative aspect rather than a restrictive aspect. The scope of the present disclosure should be defined by the claims rather than the above-mentioned description, and all differences within the scope equivalent to the claims should be interpreted to fall within the present disclosure.

What is claimed is:

1. A method for classifying patients with brain disorders based on electro encephalo graphy (EEG) analysis, the method comprising:
   (a) receiving an EEG data set input with a clinical diagnosis label, wherein the EEG data set includes a plurality of EEG signals and age information;
   (b) augmenting the EEG data set through a deep learning-based screening model, and augmenting the EEG signals and the age information in different schemes, wherein the deep learning-based screening model is a model configured by an ensemble of a plurality of different heterogeneous models;
   (c) training the deep learning-based screening model to classify EEG data of patients into a target clinical diagnosis label by using the augmented EEG signals and age information; and
   (d) predicting a brain disorder diagnosis label by applying the EEG data of patients to the trained deep learning-based screening model,
   wherein the step (b) comprises,
   randomly cropping the EEG signals to a fixed length T at a plurality of positions, and then normalizing the EEG signals by using an average and a standard deviation, wherein the EEG signals are a brain wave including artifact which is not preprocessed,
   augmenting the EEG signals by applying multiplicative white Gaussian noise (MWGN) and additive white Gaussian noise (AWGN) to the EEG signals, and
   augmenting the age information by applying the additive white Gaussian noise (AWGN) to the age information.

2. The method of claim 1, wherein the clinical diagnosis label is for normal, mild brain disorders, and dementia.

3. The method of claim 1, wherein the augmented EEG signals and age information are connected in an input layer through a single channel and applied to an encoder module, and
   the encoder module generates a feature map by applying a convolution operation to the augmented EEG signals, and the age information is connected in the feature map just before a fully connected layer of the encoder module.

4. The method of claim 1, wherein the deep learning-based screening model randomly crops the EEG signals based on an equation below:

$$\hat{\mathbb{E}}_{crop}^{train}(f_w) = \frac{1}{BN}\sum_{i=1}^{B}\sum_{i=1}^{N}\ell(f_w(x_{t:t+T}^i), y^i) \approx \frac{1}{N}\sum_{i=1}^{N}\ell\underbrace{\left(\frac{1}{M}\sum_{i=1}^{M}f_w(x_{t:t+T}^i), y^i\right)}_{test\text{-}time\ augmentation}$$

wherein, B represents the number of training epochs, $x_{t:t+T}^i$ represents the EEG signals in which an i-th EEG signal in the EEG data set is cropped to a fixed length T, $y^i$ represents the clinical diagnosis label for $x_{t:t+T}^i$, $\ell$ represents a loss function, N represents the amount of training data, and $f_w$ represents a model function having a parameter w.

5. The method of claim 1, wherein each EEG data set is constituted by 21 channels, and includes 19-channel EEG signals acquired at electrode positions of Fp1, F3, C3, P3, O1, Fp2, F4, C4, P4, O2, F7, T3, T5, F8, T4, T6, FZ, CZ, and PZ, a one-channel electrocardiogram signal, a one-channel photostimulation signal, and one-channel age information.

6. A non-transitory computer readable recording medium having a program code recorded for executing the method of claim 1.

7. An apparatus for classifying patients with brain disorders based on EEG analysis, the apparatus comprising:
  a data acquisition unit receiving an EEG data set input with a clinical diagnosis label, wherein the EEG data set includes a plurality of EEG signals and age information;
  a data augmentation unit augmenting the EEG data set, wherein the EEG signals and the age information are augmented in different schemes;
  a training unit training a deep learning-based screening model to classify EEG data of patients into a target clinical diagnosis label by applying the augmented EEG signals and age information to the deep learning-based screening model, wherein the deep learning-based screening model is a model configured by an ensemble of a plurality of different heterogeneous; and
  a diagnosis prediction unit predicting a diagnosis label by applying the EEG data of patients to the trained deep learning-based screening model,
  wherein the data augmentation unit randomly crops the EEG signals to a fixed length T at a plurality of positions, and then normalizes the cropped EEG signals by using an average and a standard deviation, augments the EEG signals by applying multiplicative white Gaussian noise (MWGN) and additive white Gaussian noise (AWGN) to the EEG signals, and augments the age information by applying the additive white Gaussian noise (AWGN) to the age information.

8. The apparatus of claim 7, wherein the training unit is trained such that the augmented EEG signals and age information are connected in an input layer through a single channel and applied to an encoder module, and
  the encoder module generates a feature map by applying a convolution operation to the augmented EEG signals, and the age information is connected in the feature map just before a fully connected layer of the encoder module and classified into the target clinical diagnosis label.

* * * * *